United States Patent
Ortmaier et al.

(10) Patent No.: US 8,965,583 B2
(45) Date of Patent: Feb. 24, 2015

(54) ROBOT, MEDICAL WORK STATION, AND METHOD FOR PROJECTING AN IMAGE ONTO THE SURFACE OF AN OBJECT

(75) Inventors: Tobias Ortmaier, Hemmingen (DE); Dirk Jacob, Augsburg (DE); Georg Passig, München (DE)

(73) Assignee: KUKA Laboratories GmbH, Augsburg (DE)

( * ) Notice: Subject to any disclaimer, the term of this patent is extended or adjusted under 35 U.S.C. 154(b) by 1306 days.

(21) Appl. No.: 12/743,688

(22) PCT Filed: Nov. 18, 2008

(86) PCT No.: PCT/EP2008/065758
§ 371 (c)(1),
(2), (4) Date: Jul. 19, 2010

(87) PCT Pub. No.: WO2009/065831
PCT Pub. Date: May 28, 2009

(65) Prior Publication Data
US 2010/0275719 A1    Nov. 4, 2010

(30) Foreign Application Priority Data

Nov. 19, 2007 (DE) .......... 10 2007 055 204

(51) Int. Cl.
*G06F 3/042* (2006.01)
*B25J 13/08* (2006.01)
(Continued)

(52) U.S. Cl.
CPC ............ *B25J 13/00* (2013.01); *A61B 19/2203* (2013.01); *G03B 21/00* (2013.01); *G06F 3/0426* (2013.01); *A61B 2017/00207* (2013.01)

USPC ............ 700/264; 700/259; 345/168; 345/175

(58) Field of Classification Search
CPC ................... A61B 19/2203; A61B 2019/2203; A61B 2017/00207; G06F 3/042; G06F 3/0425; G06F 3/0426; G06F 3/017; B25J 13/00; B25J 13/089; G05B 2219/40003
USPC ......... 700/245, 246, 250, 257, 258, 259, 264; 345/156, 168, 170, 173, 175; 361/679.21, 679.22, 679.23; 715/863

See application file for complete search history.

(56) References Cited

U.S. PATENT DOCUMENTS

| | | | | |
|---|---|---|---|---|
| 5,981,965 | A * | 11/1999 | Pryor et al. | 250/559.23 |
| 2002/0016541 | A1* | 2/2002 | Glossop | 600/407 |
| 2008/0136775 | A1* | 6/2008 | Conant | 345/156 |

FOREIGN PATENT DOCUMENTS

| | | |
|---|---|---|
| DE | 199 51 503 A1 | 1/2001 |
| EP | 1 555 507 A1 | 7/2005 |

(Continued)

OTHER PUBLICATIONS

Cassinelli et al., "Smart Laser Scanner for Human-Computer Interface," 2005, Ishikawa-Namiki Laboratory, The University of Tokyo.*

(Continued)

*Primary Examiner* — Spencer Patton
(74) *Attorney, Agent, or Firm* — Wood, Herron & Evans, LLP

(57) ABSTRACT

The invention relates to a robot (R), a medical work station, and a method for projecting an image (20) onto the surface of an object (P). The robot (R) comprises a robot arm (A) and a device (18) for projecting the image (20) onto the surface of the object (P), said device (18) being mounted on or integrated into the robot arm (A).

13 Claims, 3 Drawing Sheets

(51) Int. Cl.
   *B25J 13/00*   (2006.01)
   *A61B 19/00*   (2006.01)
   *G03B 21/00*   (2006.01)
   *A61B 17/00*   (2006.01)

(56) References Cited

FOREIGN PATENT DOCUMENTS

| | | |
|---|---|---|
| JP | 2005 165804 | 6/2005 |
| JP | 2008 006551 | 1/2008 |

OTHER PUBLICATIONS

Underkoffler, John Stephen, "The I/O Bulb and the Luminous Room", Feb. 1999, Massachusetts Institute of Technology.*
Paluska, Dan, "MIT LegLab", accessed Aug. 31, 2006, http://www.ai.mit.edu/projects/leglab/mpeg_vcd/.*
Raskar et al., "iLamps: Geometrically Aware and Self-Configuring Projectors", 2003, ACM SIGGRAPH 2003 Conference Proceedings, Mitsubishi Electric Research labs (MERL).*
European Patent Office; International Search Report in International Patent Application No. PCT/EP2008/065758 dated Jul. 24, 2009; 8 pages.

* cited by examiner

ROBOT, MEDICAL WORK STATION, AND METHOD FOR PROJECTING AN IMAGE ONTO THE SURFACE OF AN OBJECT

TECHNICAL FIELD

The invention relates to a robot, a medical work station, and a method for projecting an image onto the surface of an object.

BACKGROUND

In surgery, for example, increasing use is being made of computer-based systems that provide information to a surgeon who is operating on a living being. The information may be for example vital parameters of the living being, risk structures, or target positions for the operation. The information is portrayed for example using a display device of the information system, and the information system may include input means for the operation thereof. Because of the information portrayed by means of the display device, the attention of the surgeon must shift between the operation table and the display device, and possibly the input means.

SUMMARY

The object of the invention is therefore to specify a device that allows conditions for easier acquisition of visual information.

The problem of the invention is solved by a robot having a robot arm, and a device attached to the robot arm or integrated into the robot arm for projecting an image onto the surface of an object.

The problem of the invention is also solved by a method for projecting an image onto the surface of an object, having the following procedural step:

Projection of an image onto the surface of an object that is in particular a living being, using a device for projecting an image that is integrated into a robot arm of a robot or attached to the robot arm.

Although the method according to the invention or the robot according to the invention is intended in particular for the medical environment, non-medical applications are also conceivable, for example in the servicing, inspection and repairing of machines.

Robots in general are manipulating machines, which are equipped with useful tools for automatic handling of objects, and are programmable in a plurality of motion axes, in particular with regard to orientation, position and process sequence. Robots generally include the robot arm, which is also referred to as a manipulator, a control apparatus and possibly an effector, which may be designed for example as a gripper for gripping a tool, or, when used in medical technology, to apply a medical instrument. The manipulator or robot arm represents essentially the movable part of the robot. The robot arm has in particular a plurality of axes, which are driven for example by means of electric drives, by the control apparatus in the form of a computer.

In order to project an image onto the surface of the object, which is in particular a living being, according to the invention the device for projecting the image is integrated into the robot arm of the robot or is attached thereto. Thus it is possible to project the image onto the surface of the object in a relatively simple manner, on the basis of appropriate actuation of the robot arm. The device for projecting the image may be integrated or attached in particular in the vicinity of the so-called tool center point (TCP) of the robot. The site of the projection may be chosen for example by software.

According to one embodiment of the robot according to the invention, the latter has a device, in particular attached to the robot arm or integrated into the robot arm, for recording an image of the image projected on the surface of the object, where a data processing device, in particular of the robot, is set up to analyze a picture data record that is assigned to an image recorded using the device for recording an image, of the image projected on the surface of the object. The device for recording an image of the image projected on the surface of the object is for example a camera, or sensors, that deliver, in particular by themselves, a 2.5-D image of the surroundings. The device for recording an image may also be attached however for example to a stand, a wall or a ceiling.

If the projected image involves for example virtual input means of the data processing device, in particular of the robot, or virtual input means of some other data processing device, then according to one variant of the robot according to the invention, the data processing device in particular of the robot is set up so that it analyzes the picture data record for gestures of a person, in order to detect actuation of the virtual input means. The virtual input means may have for example virtual operating elements, portrayed on the surface of the objects by means of the projected image, where the data processing device analyzes the picture data record for example by means of pattern recognition algorithms to determine whether the person is touching the virtually portrayed operating elements. Based on the analysis of the image or picture data record, it is accordingly possible to detect the gestures of the person and to interpret them as actuation of the virtual input means. If the object is in particular the living being, for example a patient who is to be treated, then the person, who is for example a surgeon or a doctor in general, can actuate the virtual input means in the sterile environment.

According to another embodiment of the robot according to the invention, the latter has means for detecting a distortion of the projected image caused by the surface geometry of the surface of the object, which triggers the device for projecting the image so that it at least partially compensates for the distortion of the projected image. Distortion means that the display height, i.e., the distance of a pixel from the center of the projected image, depends in a non-linear way on the height of the corresponding point on the object. One can also say that the image scale depends on the height of the corresponding point on the object. An example of a result of a distortion is that straight lines whose image does not pass through the center of the projected image are reproduced as curves.

The means for detecting the distortion include, according to one variant of the robot according to the invention, the device for recording an image, in particular integrated into the robot arm or attached to the robot arm, and the data processing device, which according to this embodiment is set up to detect the distortion on the basis of the analyzed picture data record. This may be realized for example as follows: The picture data record assigned to the image of the projected image can be compared with the picture data record assigned to the projected image. That results in a stereo system to detect the distortion. The inverse representation of the projected image can then be taken into account when projecting the projected image, so that the distortion can be at least partially compensated for.

The determination of the distortion can be made for example while the image is being projected. The determination of the distortion can also be performed, however, during a process of calibrating the device for projecting the image by means of a reference image.

According to another embodiment of the robot according to the invention, the data processing device is set up so that on the basis of another previously created picture data record, in particular a three-dimensional picture data record of the object, it actuates the device for projecting the image in such a way that the latter at least partially compensates for a distortion of the projected image. If the object is the living being, then the additional picture data record of the object can be created in particular by means of a medical imaging device, for example a magnetic resonance device, a computer tomography device, an X-ray device or an ultrasound device.

The robot according to the invention is intended in particular to be used in conjunction with a medical work station. According to one embodiment of a medical work station according to the invention, the latter has, in addition to the robot according to the invention, a navigation system for detecting the positions of the living being and of the robot, with the data processing device of the robot being set up so that it actuates the device for projecting the image in such a way that the positions of the robot and of the living being are taken into account in the at least partial compensation for the distortion of the projected image. This variant of the medical work station according to the invention is accordingly designed so that the following procedural steps can be carried out in addition for the method according to the invention:

Determining the positions of the robot and of the living being, in particular by means of the navigation system, determining the anticipated distortion of the image projected onto the surface of the living being on the basis of the positions of the living being and of the robot and on the basis of a previously recorded picture data record of the living being, and at least partially compensating for the anticipated distortion of the image projected onto the surface on the basis of the positions of the robot and of the living being and on the basis of the picture data record of the living being.

Navigation systems are known in medical technology, in particular in minimally invasive medical technology, for example from DE 199 51 503 B4. Navigation systems include for example markers positioned on the robot and markers positioned on the living being or on a patient-transport trolley on which the living being is lying, and a device for detecting the markers. The device for detecting the markers is for example an optical device, such as for example a stereo camera. On the basis of the markers picked up with the device for detecting the markers, the navigation system is able to determine the positions of the robot and of the living being in an essentially generally-known manner. On the basis of the positions of the robot and of the living being, and of the picture data record, in particular three-dimensional, taken of the living being, the data processing device is able to calculate the anticipated distortion of the projected image and to adjust the device for projecting the image accordingly, so that the anticipated distortion is at least partially compensated for.

The device for detecting the markers of the navigation system can also be used to record the image of the projected image. The picture data record assigned to the image can then also be used for the means of detecting the distortion.

If the navigation system is also used during the treatment of the living being, in order to determine the position of the latter, then the partial compensation for the anticipated distortion can be updated as the patient is moved. This compensation can be carried out for example as such by the device for projecting.

According to one embodiment of the method according to the invention, however, the at least partial compensation is updated by carrying the robot arm along corresponding to the movement of the living being.

Accordingly, with the robot according to the invention or with the method according to the invention, so-called augmented reality can be applied. Augmented reality means in general computer-supported augmentation of the perception of reality.

BRIEF DESCRIPTION OF THE DRAWINGS

Examples of exemplary embodiments of the invention are depicted in the attached schematic drawings. The figures show the following.

DETAILED DESCRIPTION

Figure 1:
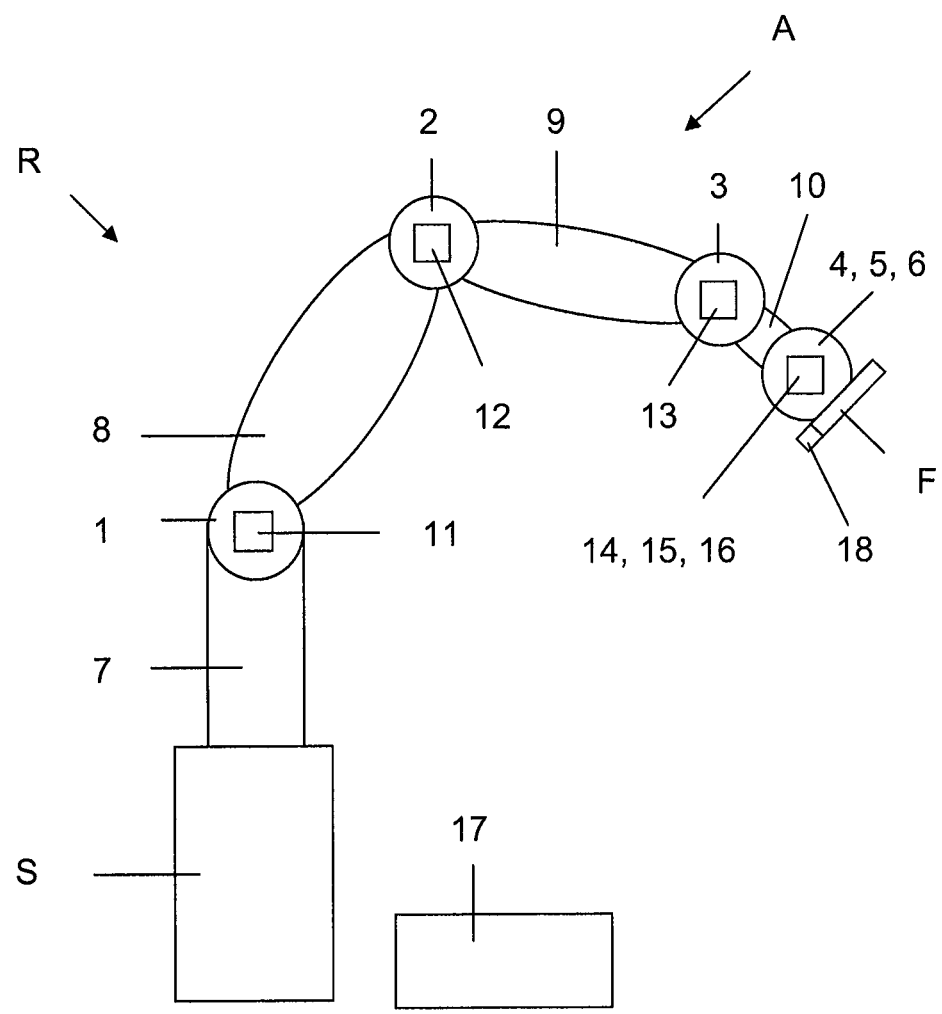
FIG. 1 a robot,
FIG. 2 a medical work station having the robot of FIG. 1,
FIG. 3 virtual input means, and
FIG. 4 a medical imaging device.

FIG. 1 shows a robot R having a robot arm A, which in the case of the present exemplary embodiment is attached to a base S. Robot arm A represents essentially the movable part of robot R, and includes a plurality of axes 1-6, a plurality of levers 7-10 and a flange F, to which for example a tool or a medical instrument may be attached.

In the case of the present exemplary embodiment, each of the axes 1-6 is moved with an electric drive, which are electrically connected in a non-depicted manner to a control computer 17 of robot R, so that control computer 17 or a computer program running on control computer 17 is able to actuate the electric drives in such a way that the position and orientation of flange F of robot R can be set essentially freely in space. The electric drives of robot R each include for example an electric motor 11-16 and possibly power electronics that actuate the motors 11-16.

In the case of the present exemplary embodiment, a projector 18 that is able to project an image onto a surface of an object is integrated into robot arm A and in particular into flange F. Alternatively, projector 18 may also be attached to the structure of robot arm A, in particular to flange F, for example also removably.

Projector 18 is electrically connected to a computer, for example to control computer 17, in a manner that is not shown.

Figure 2:
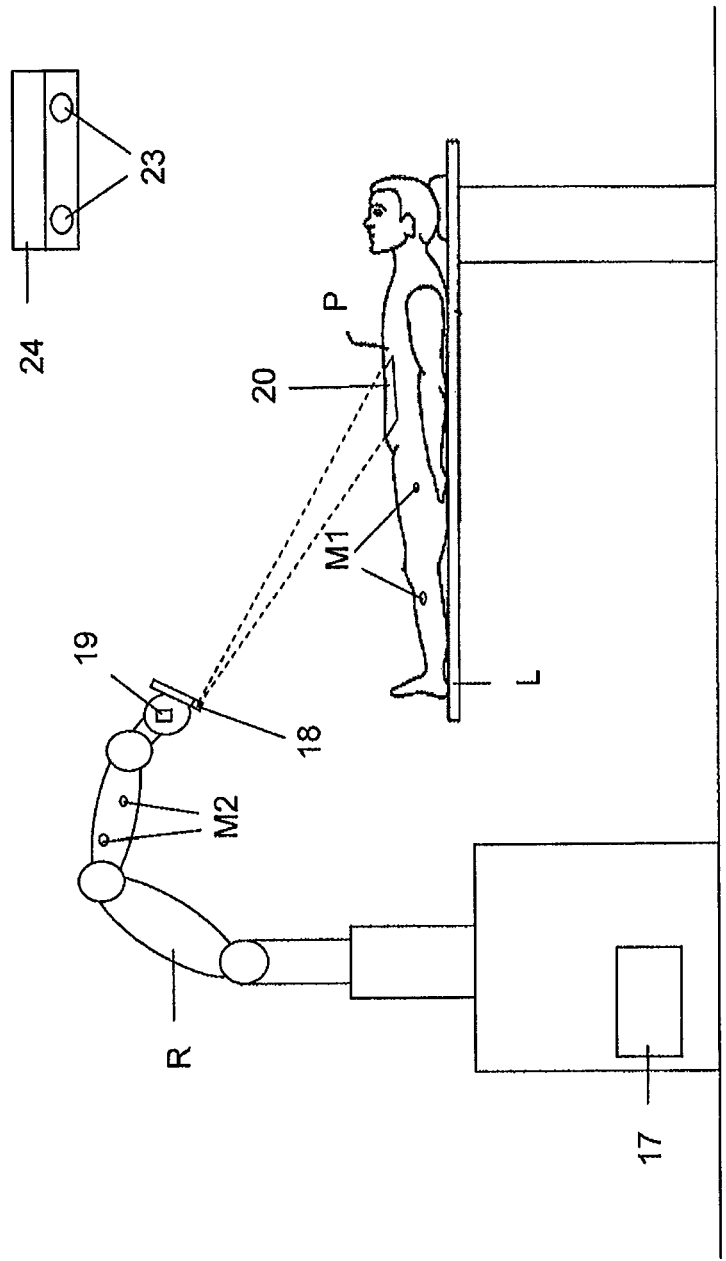

In the case of the present exemplary embodiment, robot R is intended to be part of a medical work station depicted in FIG. 2.

The medical work station depicted in the case of the present exemplary embodiment includes, in addition to robot R, a patient-transport trolley L, which may also be height-adjustable, and a navigation system. Patient-transport trolley L is provided so that a patient P depicted in FIG. 2 may lie on it. The patient may be operated on by a surgeon, not depicted in FIG. 2.

Robot R is provided in the case of the present exemplary embodiment to project an image 20 by means of its projector 18 onto the surface of patient P.

Figure 3:
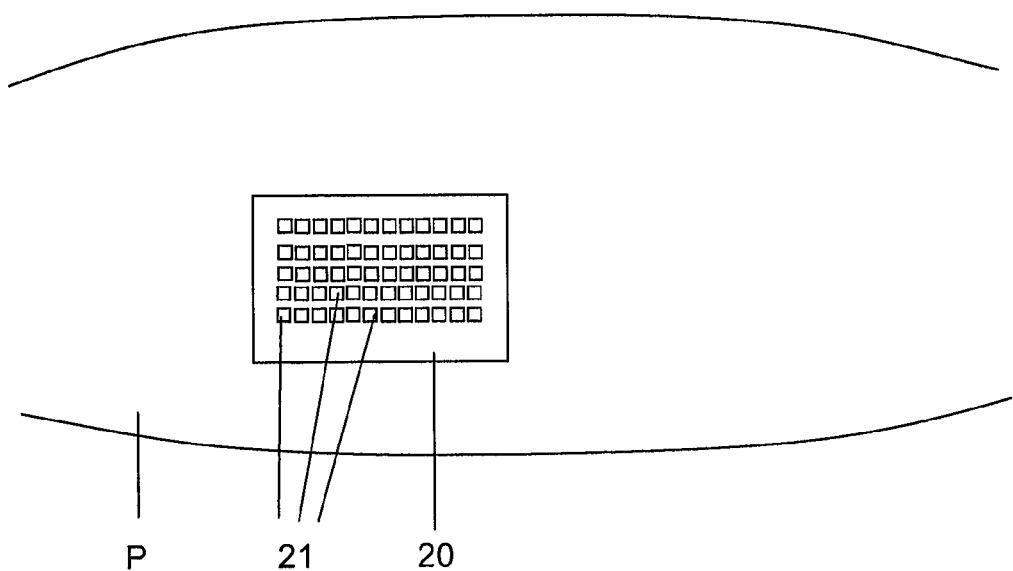

In the case of the present exemplary embodiment, projected image 20, which is shown in greater detail in FIG. 3, represents input means for control computer 17 or for some other data processing system, not shown in greater detail in the figures, and has for example the form of a keyboard. The virtual input means in the form of projected image 20 also include virtual operating elements 21, which correspond for example to the keys of an actual keyboard.

In the case of the present exemplary embodiment, robot R includes in addition a camera 19 that is electrically connected to control computer 17, and that is integrated into robot arm A or attached thereto. Camera 19 is oriented so that it records an image of the image 20 projected onto patient P. The picture data record assigned to the image of projected image 20 is analyzed by means of pattern recognition algorithms by control computer 17 or by a computer program running on control computer 17, to determine whether a person who is not depicted in the figures, for example the surgeon who is operating on patient P, is actuating the virtual operating elements 21 of the virtual input means depicted in the form of projected image 20. If the computer program running on control computer 17 detects, on the basis of the aforementioned picture data record, that the surgeon for example is touching the area of one of the virtual operating elements 21, the computer program running on control computer 17 triggers a reaction assigned to the actuation of that virtual operating element 21.

Projected image 20 exhibits distortion due to the curved surface of patient P. This is compensated for at least partially in the case of the present exemplary embodiment by the fact that before image 20 is projected onto patient P a reference image, not shown in greater detail, is projected onto patient P with projector 18. The reference image is projected essentially onto the same place on the surface of patient P onto which image 20 is also projected.

An image of the projected reference image is then recorded with camera 19, and the picture data record assigned to this image is analyzed with another computer program running on control computer 17. On the basis of the picture data record assigned to the image of the projected reference image and a target representation of the projected reference image, control computer 17 can actuate projector 18 so that the latter at least partially compensates for any distortion of the projected image 20 that is to be portrayed later.

Figure 4:
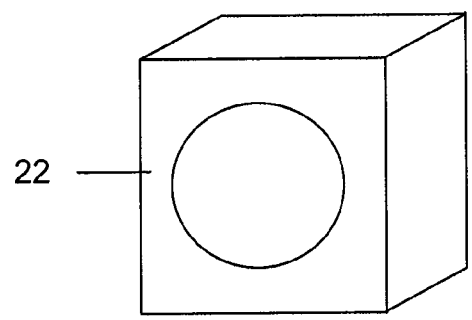

In another embodiment, prior to the operation on patient P, a picture data record, in particular a three-dimensional one, has been created by means of a medical imaging apparatus 22 depicted in FIG. 4. The medical imaging apparatus 22 is for example a magnetic resonance device, a computer tomography device, an X-ray device, for example a C-arm X-ray device, or an ultrasound device.

The three-dimensional picture data record created from patient P can be used for example for diagnosing patient P, and is read into control computer 17 of robot R. On the basis of the positions of robot R and of patient P, as well as on the basis of the three-dimensional picture data record of patient P, an additional computer program running on control computer 17 can determine an anticipated distortion of projected image 20, and thereby modify the projection of projector 18 so that the anticipated distortion of projected image 20 is at least partially compensated for.

The above-named navigation system is used to determine the positions of robot R and patient P. Navigation systems are known in general to the person skilled in the art, and include for example a stereo camera 23, reference marks M1 positioned on patient P and reference marks M2 positioned on robot R. To determine the positions of robot R and patient P, stereo camera 28 takes pictures of the reference marks M1, M2, whose assigned picture data records are evaluated in a generally known manner by means of a computer 24 of the navigation system. Furthermore, computer 24 of the navigation system is connected to control computer 17 of robot R in a manner not shown, so that information about the position of robot R, in particular its projector 18, and the position of patient P is available to control computer 17.

In the case of the present exemplary embodiment, there is also provision for correcting a changing distortion of projected image 20 due to a movement of patient P, for example by projector 18 being adjusted on the basis of the detected movement or the changed position of patient P due to the movement, or robot arm A being carried along with the movement of patient P in such a way that the changing distortion is at least partially compensated for.

What is claimed is:

1. A robot comprising:
   a robot arm;
   a projector supported by the robot arm and configured to project an image onto the surface of an object;
   a controller configured to process data associated with the image projected by the projector;
   a recording device configured to record an image of the image projected by the projector, the controller being further configured to analyze at least one of (a) a picture data record assigned to the image recorded by the recording device or (b) the image projected by the projector onto the surface of the object; and
   a detector configured to detect a distortion of the image projected by the projector onto the surface of the object due to a surface geometry of the object, wherein, in response to detection of the distortion, the controller actuates the projector to at least partially compensate for the detected distortion;
   wherein the controller is configured to correct for a changing distortion of the image projected by the projector due to a movement of the object;
   wherein the image projected by the projector defines a virtual input feature for the controller, the controller being configured to analyze the picture data record for a gesture of a user of the robot to thereby detect actuation of the virtual input feature;
   wherein actuation of the virtual input feature comprises the user touching the virtual input feature projected onto the surface of the object; and
   wherein the object is a living being.

2. The robot of claim 1, wherein:
   the detector is supported by the robot arm;
   the recording device and the controller form part of the detector; and
   the controller is configured to detect the distortion based on the analyzed picture data record.

3. The robot of claim 1, wherein the controller actuates the projector to project an image adjusted to at least partially compensate for a distortion of the image projected by the projector onto the surface of the object due to a surface geometry of the object based on a previously generated picture data record of the object.

4. The robot of claim 3, wherein the previously generated picture data record is a three-dimensional picture data record of the object.

5. The robot of claim 3, wherein:
   the previously generated picture data record of the object was generated by a medical imaging device.

6. A medical work station to treat a living being, comprising:
   a robot including a robot arm and a projector supported by the robot arm, the projector being configured to project an image onto the surface of the living being;
   a navigation apparatus configured to detect a position of the living being and a position of the robot;

a detector for detecting a distortion of the image projected by the projector onto the surface of the living being due to a surface geometry of the living being; and a controller configured to actuate the projector to at least partially compensate for the detected distortion based on (a) a previously generated picture data record of the living being and (b) the detected positions of the living being and of the robot, wherein the controller is further configured to correct for a changing distortion of the image projected by the projector due to a movement of the living being;

wherein the image projected by the projector defines a virtual input feature for the controller, the controller being further configured to analyze a picture data record assigned to an image of the projected image for a gesture of a user of the robot to thereby detect actuation of the virtual input feature; and wherein actuation of the virtual input feature comprises the user touching the virtual input feature projected onto the surface of the living being.

7. The medical work station of claim 6, wherein the navigation apparatus includes:

a first plurality of markers positioned on the robot;

a second plurality of markers positioned on the surface of the living being; and a marker detection device configured to detect at least one of the first or second pluralities of markers.

8. The medical work station of claim 7, further comprising:

a patient support for supporting the living being thereon, the navigation apparatus including a third plurality of markers on the patient support, the marker detection device being configured to detect the third plurality of markers.

9. The medical work station of claim 7, wherein:

the marker detection device is configured to record the image projected onto the living being, and the controller is configured to analyze a picture data record assigned to the image recorded by the marker detection device.

10. A method for projecting an image onto the surface of an object, the method comprising:

moving a robot arm of a robot relative to the object;

projecting an image, with a projector supported by the robot arm, onto the surface of the object;

recording an image associated with the image projected onto the surface of the object with a camera supported by the robot arm, the projected image defining a virtual input feature for a computer controlling the recording of the image associated with the projected image;

determining a distortion of the projected image;

compensating for the determined distortion of the projected image;

detecting movement of the object;

adjusting the compensation for the determined distortion based on the detected movement of the object; and analyzing a picture data record assigned to the recorded image for a gesture made by a user, to thereby detect actuation of the virtual input feature;

wherein actuation of the virtual input feature comprises the user touching the virtual input feature projected onto the surface of the object; and wherein the object is a living being.

11. The method of claim 10, further comprising:

determining a position of the robot and a position of the object; and recording a picture data record of the object;

wherein determining the distortion comprises determining an anticipated distortion of the image projected onto the surface of the object based on (a) the determined positions of the robot and of the object, and (b) the recorded picture data record of the object.

12. The method of claim 10, wherein adjusting the compensation for the determined distortion includes moving the robot arm based on the detected movement of the object.

13. The method of claim 10, the method further comprising:

recording a picture data record of the object with a medical imaging device.

* * * * *